United States Patent
Richardson et al.

(10) Patent No.: US 10,774,302 B2
(45) Date of Patent: Sep. 15, 2020

(54) DEVICE AND METHOD FOR DISSECTING AND ANALYZING INDIVIDUAL CELL SAMPLES

(71) Applicant: BIOSYNTAGMA, LLC, Scottsdale, AZ (US)

(72) Inventors: David Wayne Richardson, Chandler, AZ (US); Dmitry Derkach, Gibert, AZ (US); Colleen Ziegler, Tempe, AZ (US); Steve Pemberton, Bedford, NH (US)

(73) Assignee: BIOSYNTAGMA, LLC, Scottsdale, AZ (US)

( * ) Notice: Subject to any disclaimer, the term of this patent is extended or adjusted under 35 U.S.C. 154(b) by 184 days.

(21) Appl. No.: 16/086,983

(22) PCT Filed: Mar. 28, 2017

(86) PCT No.: PCT/US2017/024532
§ 371 (c)(1),
(2) Date: Sep. 20, 2018

(87) PCT Pub. No.: WO2017/172762
PCT Pub. Date: Oct. 5, 2017

(65) Prior Publication Data
US 2019/0106671 A1 Apr. 11, 2019

(51) Int. Cl.
*G01N 15/14* (2006.01)
*G01N 1/28* (2006.01)
(Continued)

(52) U.S. Cl.
CPC ........... *C12M 47/04* (2013.01); *B01L 3/5027* (2013.01); *B01L 3/502715* (2013.01);
(Continued)

(58) Field of Classification Search
CPC ..... B01L 2300/0816; B01L 2300/0861; B01L 2300/0864; B01L 2300/123;
(Continued)

(56) References Cited

U.S. PATENT DOCUMENTS 8,114,646 B2  2/2012 Martin et al.
2005/0244301 A1* 11/2005 Fletcher ............. A61B 17/3203
                                                              422/400

(Continued)

OTHER PUBLICATIONS

Rosell, Mateo A., "Supplementary European Search Report"; date of completion of the search Oct. 7, 2019 for application No. PCT/US2017/24532; European Patent Office, Berlin, Germany.
(Continued)

*Primary Examiner* — Jennifer Wecker
(74) *Attorney, Agent, or Firm* — Woods Oviatt Gilman LLP; Ronald J. Kisicki, Esq.; Dennis B. Danella, Esq.

(57) ABSTRACT

A method for dissecting and collecting one or more cells from a tissue sample fixed to an inner surface of a microfluidic device is described. The tissue sample is in fluid communication with a channel having an inlet end and an outlet end defined by the microfluidic device. The method comprises flowing a first fluid through the channel with a fluid flow from the inlet end to the outlet end; powering a laser to direct laser energy into the channel to impinge upon the first fluid proximate a first region of the tissue sample and cause fluid cavitation to thereby ablate a first set of one or more cells from the tissue sample; and collecting the first set of one or more cells within a first sample container coupled to the outlet end.

27 Claims, 15 Drawing Sheets

(51) Int. Cl.
*G01N 1/44* (2006.01)
*C12M 1/00* (2006.01)
*C12M 1/14* (2006.01)
*B01L 3/00* (2006.01)
*G16B 50/00* (2019.01)
*G01N 15/10* (2006.01)

(52) U.S. Cl.
CPC ............... *C12M 1/00* (2013.01); *C12M 1/14* (2013.01); *G01N 1/286* (2013.01); *G01N 15/1463* (2013.01); *G16B 50/00* (2019.02); *B01L 2300/0816* (2013.01); *B01L 2300/0861* (2013.01); *B01L 2300/0864* (2013.01); *B01L 2300/123* (2013.01); *B01L 2400/0481* (2013.01); *B01L 2400/0487* (2013.01); *G01N 2001/2886* (2013.01); *G01N 2015/1006* (2013.01); *G01N 2015/1497* (2013.01)

(58) Field of Classification Search
CPC ..... B01L 2400/0481; B01L 2400/0487; B01L 3/5027; B01L 3/502715; C12M 1/00; C12M 1/14; C12M 47/04; G01N 15/1463; G01N 1/286; G01N 2001/2886; G01N 2015/1006; G01N 2015/1497; G16B 50/00
See application file for complete search history.

(56) References Cited

U.S. PATENT DOCUMENTS

| | | |
|---|---|---|
| 2008/0114386 A1 | 5/2008 | Iliakis et al. |
| 2010/0221752 A2 | 9/2010 | Gold et al. |
| 2010/0285992 A1 | 11/2010 | Wang et al. |
| 2015/0197720 A1 | 7/2015 | Chiou et al. |
| 2015/0313759 A1 | 11/2015 | Vera et al. |
| 2016/0068798 A1* | 3/2016 | Yoon ................ C12Q 1/24 506/2 |

OTHER PUBLICATIONS

Hyoung Won Baac, et al.; "Micro-ultrasonic cleaving of cell clusters by laser-generated focused ultrasound and its mechanisms"; Biomedical Optics Express, vol. 4, No. 8; Jul. 26, 2013; pp. 1442-1450; XP055629313, United States.

Zwaan, Ed, et al.; "Controlled Cavitation in Microfluidic Systems"; Physical Review Letters, vol. 98, No. 25; Jun. 1, 2007; pp. 254501-1-254505-4; XP055629316, United States.

Schaerli, Yolonda, et al.; "The potential of microfluidic water-in-oil droplets in experimental biology"; Molecular BioSystems, vol. 5, No. 12; Jan. 1, 2009; pp. 1392-1404; XP055270349, Great Britain.

Chen, Ran, et al.; "Controllable microfluidic production of gas-in-oil-in-water emulsions for hollow microshperes with thin polymer shells"; Lab on a Chip, vol. 12, No. 20; Jan. 1, 2012; p. 3858; XP055629464.

Chen, Yan, et al; "An automated microfluidic device for assessment of mammalian cell genetic stability"; Molecular BioSystems, vol. 12, No. 20; Jan. 1, 2012; pp. 1-11; XP055192953.

Shah, Rhutesh K.; "Designer emulsions using microfluidics"; Materials Today, vol. 11, No. 4; Mar. 15, 2008; pp. 18-27; XP022535514, Elsevier, Amsterdam, NL.

Young, Lee W., "PCT International Search Report", dated Jun. 19, 2017 for application No. PCT/US2017/24532, U.S. Patent Office, Alexandria, VA 22313-1450.

Young, Lee W., "Written Opinion of the International Searching Authority", dated Jun. 19, 2017 for application No. PCT/US2017/24532, U.S. Patent Office, Alexandria, VA 22313-1450.

* cited by examiner

DEVICE AND METHOD FOR DISSECTING AND ANALYZING INDIVIDUAL CELL SAMPLES

CROSS REFERENCE TO RELATED APPLICATIONS

This application is a National Stage filing under 35 U.S.C. § 371 of International Application No. PCT/US2017/024532, filed Mar. 28, 2017, which claims the benefit of U.S. Provisional Patent Application No. 62/390,431, filed Mar. 29, 2016, which is hereby incorporated by reference in its entirety.

TECHNICAL FIELD

This invention generally relates to methods for isolating, dissecting, collecting, sorting and analyzing individual cells or groups of cells from fresh, frozen, or fixed biological laboratory samples; and more particularly to isolating, dissecting, collecting, sorting and analyzing individual cells or groups of cells from biological laboratory samples formalin-fixed in paraffin; still more particularly to the conservation and visualization of spatial and morphological information of the dissected and collected individual cells or groups of cells.

BACKGROUND OF THE INVENTION

Current methods to isolate individual cells from formalin-fixed paraffin-embedded (FFPE) tissue samples lack out-of-plane (z-axis) resolution. These techniques typically utilize laser capture microdissection (LCM) to detach cells glued to a plastic film or a glass plate (x-y plane) either by heat through use of a pulsed infrared laser (see e.g., the PixCell II infrared LCM system commercialized by Arcturus Engineering of Mountain View, Calif., US), or by force against gravity using ultraviolet laser capture microdissection (see e.g., the Palm Zeiss ultraviolet LCM system commercialized by P.A.L.M. Microlaser Technologies AG of Bernried, Germany). Each of these systems are dry systems where the laser energy impinges upon the tissue sample to ablate cells and cell material. The recovery rate of ablated cells is very low and the direct impingement of the laser on the tissue may potentially damage the cells and chemical/structural constituents thereof, thereby negatively impacting study analysis and results. Also, these LCM techniques require the use of an Eppendorf micro-centrifuge-tube which greatly restricts throughput. Moreover these techniques are restricted to two-dimensional (2-D) analysis and cannot be used with samples having layers of cells in the z axis. In other words, traditional LCM approaches are restricted to the x-y plane and lack out-of-plane resolution in the z axis.

One attempt to address the above shortcomings of traditional LCM techniques is to couple a microfluidic device with the laser source. The microfluidic device holds the tissue sample within a chamber and a fluid flows through the chamber where the laser directly impinges upon the tissue sample. One or more cells may be ablated from the tissue sample upon laser impingement. The ablated cells are then received in and carried by the fluid flow to a sample collecting element. Cells may be serially ablated and collected in respective collecting elements. Each respective collecting element may be used to maintain spatial information regarding the collected cells. In this manner, the tissue sample may be interrogated across the x-y plane in a first instance. The laser can then be used to ablate the next successive layer in similar fashion. All of the above cell samples may then be analyzed and any data collected may be correlated to locate the spatial location of the respective cell sample within the entire original tissue sample. However, while achieving resolution in the z-axis with improved sampling efficiencies, direct laser impingement upon the tissue sample may cause damage to the ablated cells or the underlying cell layer of the tissue sample thus negatively impacting any information collected or reported study results.

Accordingly, what is needed in the art is a device and method for isolating, dissecting, collecting, sorting and analyzing individual cells or groups of cells without direct laser impingement upon the tissue sample, as well as the conservation of spatial and morphological information of individual cells or cell groups to enable visualization, recordation and study through multimodal molecular analysis of quantum dissected qubits of tissue voxels.

SUMMARY OF THE INVENTION

Briefly described, a method for dissecting and collecting one or more cells from a tissue sample fixed to an inner surface of a microfluidic device where the tissue sample is in fluid communication with a channel having an inlet end and an outlet end defined by the microfluidic device comprises flowing a first fluid through the channel with a fluid flow from the inlet end to the outlet end; powering a laser to direct laser energy into the channel to impinge upon the first fluid proximate a first region of the tissue sample and cause fluid cavitation to thereby ablate a first set of one or more cells from the tissue sample; and collecting the first set of one or more cells within a first sample container coupled to the outlet end. Ablation of the tissue sample may be optically monitored using a microscope.

In a further aspect of the present invention, the method may further include flowing a second fluid within the channel wherein the first fluid forms discretized fluid slugs comprised of the first fluid. To that end, the laser may be powered when a respective fluid slug of the first fluid communicates with the first region of the tissue sample and may be unpowered when a respective wash droplet communicates with the first region of the tissue sample. In one aspect of the invention, the first fluid is an oil and the second fluid is a gas, while in another aspect, the first fluid is an oil and the second fluid is a liquid immiscible with the oil.

In another aspect of the present invention, the method may further include injecting a third fluid within the channel wherein the third fluid forms discretized wash droplets comprised of the third fluid. The wash droplets may be interposed between successive fluid slugs of the first fluid. The first fluid may be an oil, the second fluid may be a gas and the third fluid may be a liquid immiscible with the oil.

In still another aspect of the present invention, the channel may be a serpentine channel including alternating linear channel segments and curved channel segments with the linear channel segments arranged in parallel relation to one another. Each linear channel is configured to overlap a portion of the tissue sample. Alternatively, the microfluidic device may define a plurality of channels arranged in spaced parallel relation. Each channel may include a respective inlet end and outlet end and each channel may be configured to overlap a portion of the tissue sample. Fluid flow may be through one channel of the plurality of channels at a time.

In still a further aspect of the present invention, the microfluidic device may further comprise a planar bottom slide affixed to a microfluidic substrate thereby defining the channel therebetween. The channel has a length, width and depth wherein the resilient member is configured to be addressable to selectively reduce at least a portion of the width of the channel. In one aspect, the resilient membrane may be addressable by a plunger, where the plunger may be actuatable to direct the resilient membrane in touching engagement with the planar bottom slide. Alternatively, the resilient membrane may be covered by a top cover opposite the planar bottom slide. The resilient membrane may define a membrane channel where the membrane channel may be actuatable to direct the resilient membrane in touching engagement with the planar bottom slide.

In yet another aspect of the present invention, the channel may overlap with more than one tissue sample. The laser may then be powered to impinge the first fluid proximate only one tissue sample at a time.

In still another aspect of the present invention, the method may further include the additional step of infusing a solution containing nanoparticles selected to absorb the laser energy prior to powering the laser. The nanoparticles may penetrate a portion of the tissue sample to form a nanoparticle saturated tissue layer and the laser energy may be directed to the nanoparticle saturated tissue layer whereby the nanoparticles absorb the laser energy and ablate the first set of one or more cells from the tissue sample. Additionally or alternatively, a target cell within the tissue sample may be selectively labeled with a fluorescent dye or biomarker to produce a labeled cell. The laser energy may be directed to the first fluid proximate the labeled cell thereby causing fluid cavitation and ablation of the labeled cell from the tissue sample.

In yet a further aspect of the present invention, the method may further include the steps of powering the laser to direct laser energy into the channel to impinge upon the first fluid proximate a second region of the tissue sample and cause fluid cavitation to thereby ablate a second set of one or more cells from the tissue sample; and collecting the second set of one or more cells within a second sample container coupled to the outlet end. The first sample container and second sample container may be respective wells within a multi-well plate. A further step may be effectuating relative movement between the microfluidic device and the laser after collecting the first set of one or more cells within the first sample container and before powering the laser to direct laser energy into the channel to impinge upon the first fluid proximate a second region of the tissue sample.

Further steps may include uniquely identifying the first and second sample containers to conserve spatial and/or morphological information of the respective first and second sets of one or more cells relative to the fixed tissue sample; storing the spatial and/or morphological information of the respective first and second sets of one or more cells within in a database; performing molecular analysis on one or both of the first and second sets of one or more cells to create cell data; correlating the cell data with the respective spatial and/or morphological information of the respective first and/or second sets of one or more cells to create a compiled data file for each cell or group of cells within the first and second sets of one or more cells; retrieving at least one of the spatial and/or morphological information, the cell data or the compiled data from the database; and electronically reconstructing at least a portion of the tissue sample using at least one of the spatial and/or morphological information, the cell data and the compiled data. The database may be resident within a cloud and the spatial and/or morphological information, the cell data and the compiled data may be stored in the cloud and retrieved from the cloud through a network.

Additional objects, advantages and novel features of the present invention will be set forth in part in the description which follows, and will in part become apparent to those in the practice of the invention, when considered with the attached figures.

BRIEF DESCRIPTION OF THE DRAWINGS

The above-mentioned and other features are advantages of this invention, and the manner of attaining them, will become apparent and be better understood by reference to the following description of the invention in conjunction with the accompanying drawings, wherein.

DETAILED DESCRIPTION

Figure 1:
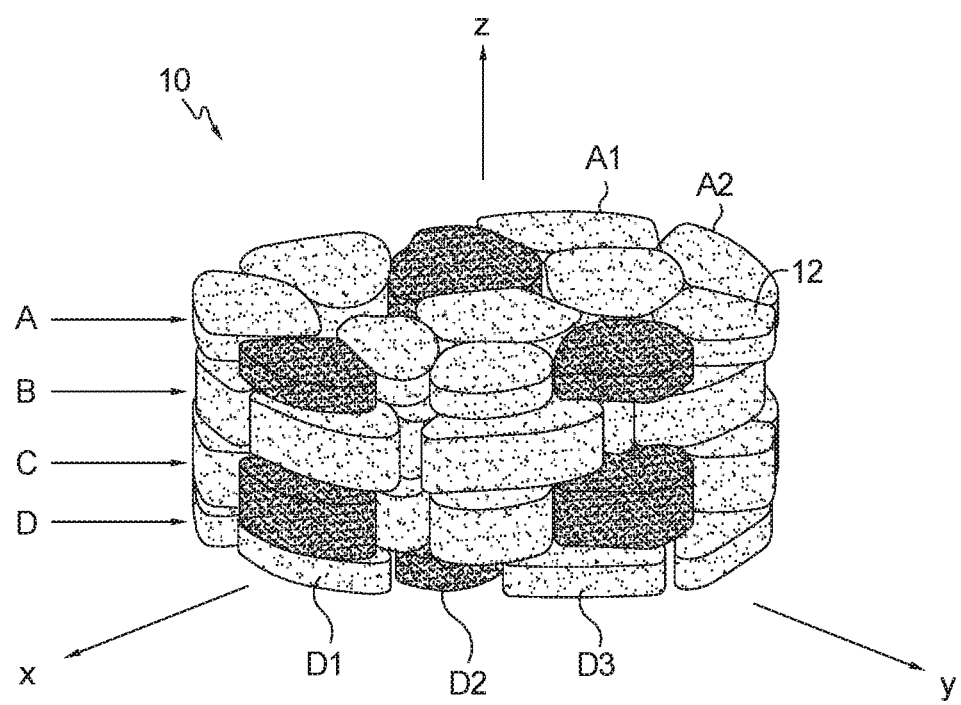
FIG. 1 is an isometric view of an exemplary tissue sample, the tissue sample may be a histological formalin-fixed paraffin-embedded (FFPE) tissue sample.

Attention is now turned to FIG. 1, which by assembly illustrates a cluster of cells 12 in an exemplary formalin-fixed paraffin-embedded (FFPE) tissue sample 10. Cells 12 are in layers in tissue 10 with the layer extension measured in x and y directions and the layer thickness in direction z. Tissue 10 has cell layers A, B, C and D whereby individual cells 12 in any particular cell layer are numbered as cell layer/cell number, such as A1, A2, etc., and D1, D2, D3, etc. Laser capture microdissection (LCM) strips or captures the top layer of cells first (i.e., cell layer A). Ideally, the newly exposed second layer (i.e., cell layer B) would be captured next, and so on in direction z. However, only cell layer A can typically be removed as traditional LCM methods cause damage to cell layer B, thereby rendering the underlying cells unsuitable for capture and analysis. Thus, LCM is not sensitive to direction z, and as such, it is unsuitable to preserve 3-D information (x-y-z) of individual cells in a tissue sample. LCM, therefore, operates on 2-D layers (x-y), which is a significant drawback to tumor cell recognition and morphology studies. As discussed in greater detail below, aspects of the present invention seek to overcome this shortcoming, as well as provide additional benefits.

Figure 2:
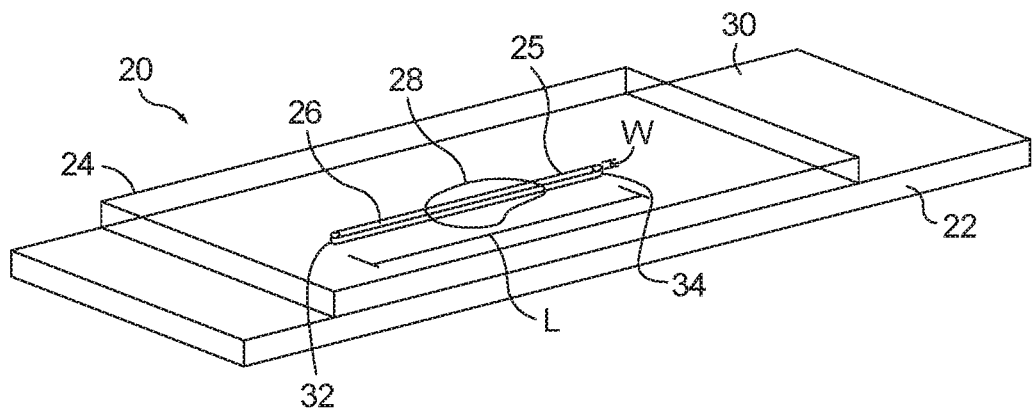
FIG. 2 is an isometric view of an exemplary embodiment of the invention with a single microfluidic channel.
Figure 3:
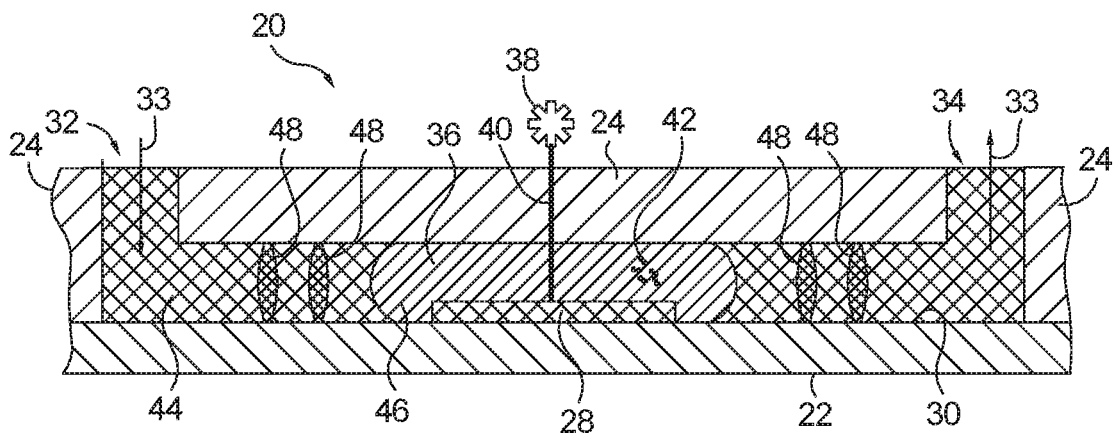
FIG. 3 is a diagrammatic section view of an exemplary microfluidic channel in operation with a single tissue.

Turning now to FIGS. 2 and 3, an exemplary embodiment of a microfluidic device in accordance with an aspect of the invention is generally indicated by reference numeral 20. Microfluidic device 20 may generally comprise a bottom planar slide, such as glass slide 22, compressed, adhered, bonded or otherwise coupled to microfluidic substrate 24. A recess 25 may be fabricated within microfluidic substrate 24 whereby a channel 26 may be formed upon coupling glass slide 22 to microfluidic substrate 24. Channel 26 may be fabricated to have a width W (FIG. 2) between about 50 micron and about 500 micron, a depth D (FIG. 3) between about 50 micron and about 500 micron, and a length L (FIG. 2) between about 2 cm and about 10 cm. A tissue sample 28 may be fixed to inner surface 30 of glass slide 22 such that at least a portion of tissue sample 28 is in communication with channel 26. Channel 26 may further include an inlet end 32 and outlet end 34 defined within microfluidic device 20 whereby a first fluid 36 may be introduced at inlet end 32 to flow in a fluid flow (generally indicated by arrows 33) through channel 26 (and thereby communicate with tissue sample 28) before exiting out of outlet end 34. To that end, a sample container (see e.g., FIG. 18 wherein sample container is a respective well A1, etc. within a 96-well plate 180) may be coupled to outlet end 34 so as to receive and store the exiting fluid for offline analysis.

As seen more clearly in FIG. 3, a laser 38 may direct laser energy 40 into channel 26 to impinge upon first fluid 36 proximate tissue sample 28, such as within about 100 nm to about 1 micron of the surface of tissue sample 28. In one aspect of the invention, laser 38 may be a pulsing two photon infrared laser having a wavelength between about 750 nm and about 1200 nm, and more particularly between about 800 nm and about 850 nm. In a further aspect of the invention, laser 38 may be a pulsing two photon ultraviolet (UV) laser having a wavelength between about 200 nm and about 400 nm, and more particularly between about 300 nm and 350 nm. Laser energy 40 may operate to cause cavitation of first fluid 36 such that one or more cells 42 may be ablated from tissue sample 28. It should be noted that, while UV radiation may damage biological tissues, and more specifically DNA and RNA which absorb wavelengths within the UV spectrum, such damage is greatly reduced, and potentially eliminated, when employing a method in accordance with the present invention. That is, UV laser energy may be selectively targeted so as to impinge upon first fluid 36 and not tissue sample 28. In this manner, cells 42 may be hydrodynamically ablated from tissue sample 28 via cavitation bubbles rather than direct impingement of laser energy 40 on tissue sample 28. As a result, tissue sample 28 may be exposed to little or no UV radiation thereby decreasing the breadth and magnitude of any subsequent sample damage, if any. Accordingly, the present invention may recover better quality cell (e.g., DNA and/or RNA) samples, and resultant data, than traditional UV laser microdissection techniques.

Following ablation from tissue sample 28, cells 42 may then be captured within first fluid 36 for transport to outlet end 34, and resultant collection by the sample container coupled thereto. The laser energy does not directly impinge upon the tissue sample, and as a result, higher power laser pulses may be used without damaging cells or cell structures than are typically used in laser microdissection techniques. The collected cells 42 may then be further interrogated offline, such as through multimodal molecular analysis which will be discussed in greater detail below. While shown and described in FIG. 3 as being directed through microfluidic substrate 24 in a top-down direction, laser 38 may also be directed through glass slide 22 in a bottom-up direction. To that end, both glass slide 22 and microfluidic substrate 24 may be transparent to laser 38. Further, ablation of the tissue sample 28 may be optically monitored using a microscope (not shown) and may also be transparent to white light. In a further aspect of the present invention, there may be relative movement between microfluidic device 20 and laser 38 after collecting a first set of cells within a dedicated container and before powering laser 38 to impinge upon the fluid and ablate a second set of cells that may be collected in a second, dedicated sample container. In this manner, the microfluidic device may be rastered relative to laser 38 such that multiple regions of the sample may be collected within channel 26 with each individual region being individually sequestered so as to minimize or eliminate cross contamination.

As further shown in FIG. 3, in accordance with another aspect of the present invention, a second fluid 44 may flow within channel 26 whereby the first fluid creates discretized fluid slugs 46 of first fluid. In this aspect, first fluid 36 may be an oil while second fluid 44 is a gas or fluid immiscible within first fluid 36, and more particularly, second fluid 44 may be a gas (such as, but not limited to $N_2$). First fluid 36 may form a series of discrete fluid slugs 46 such that laser 38 may be powered when a respective fluid slug 46 of first fluid 36 communicates with tissue sample 28. Laser 38 may then be unpowered when second fluid 44 (i.e., gas) communicates with tissue sample 28. As further shown in FIG. 3, a third fluid 48 may also be injected within inlet end 32. Third fluid 48 may be comprised of detergent that is immiscible with first fluid 36 and/or second fluid 44. Third fluid 48 may operate to wash of otherwise sweep debris from channel 26 in between respective fluid slugs 46. Third fluid 48 may be discarded at outlet end 34. In this manner, ablated cells 42 may be sequestered exclusively within fluid slugs 46 where each respective fluid slug 46 may be collected within a respective, dedicated sample container which correlates to a specific laser pulse and cavitation event. As such, cross contamination of cells 42 within serial fluid slugs 46 may be reduced or eliminated.

Figure 4:
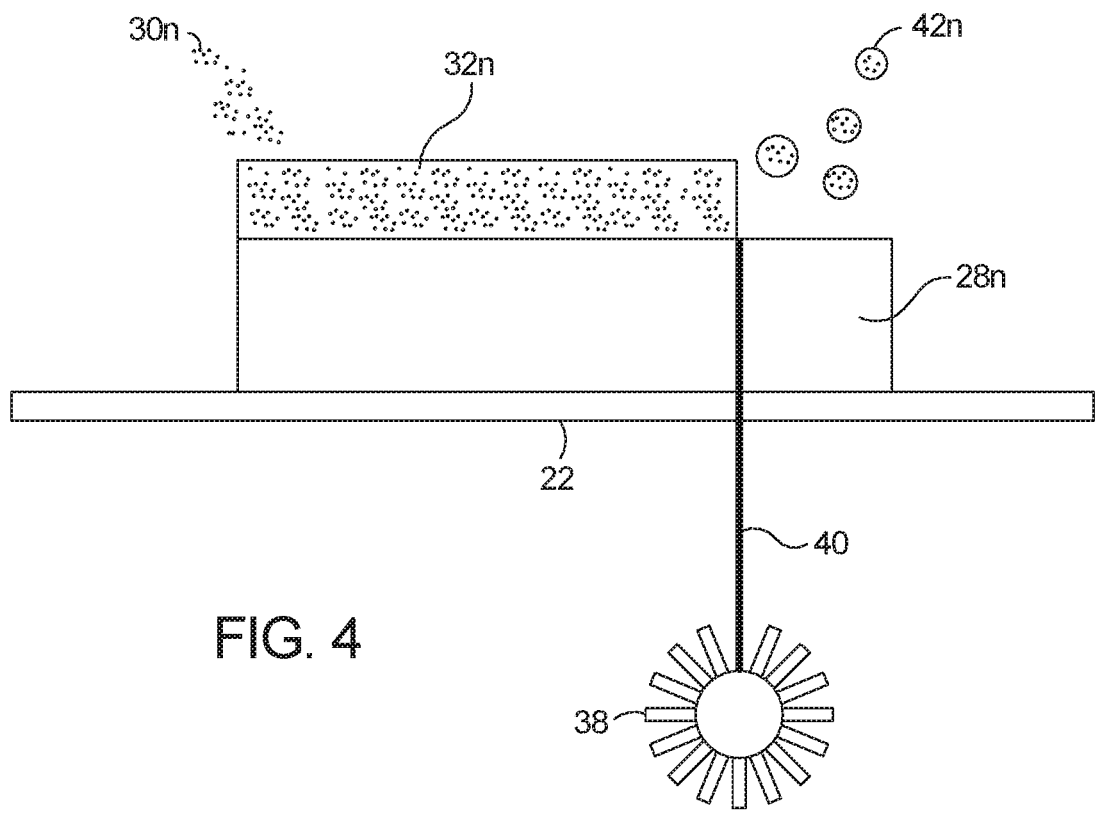
FIG. 4 is a diagrammatic section view of an exemplary z-axis controlled selective laser ablation process assisted by nanoparticle dyes.

To promote laser target location and/or laser energy absorption, tissue sample 28 may be conditioned with one or both of a nanoparticle solution tuned to absorb laser energy and a solution containing fluorescent dye and/or biomaterials configured to selectively bind with specific regions within the sample. As shown in FIG. 4, a sample 28$n$ may be affixed to glass slide 22 as generally described above. A solution containing nanoparticles 30$n$ may entrain sample 28$n$ at a specific depth so as to form a nanoparticle saturated layer 32$n$. Nanoparticles 30$n$ are tuned to absorb laser energy 40 from laser 38. The energy-absorbed portion of nanoparticle saturated layer 32$n$ may then ablate one or more cells 42$n$ which then are transported and collected as described above. Laser energy is absorbed by the nanoparticles and not by the cells such that little to no cell damage results from the laser impingement. Additionally, or alternatively, a fluorescent dye or biomarker solution may be entrained to a sample, such as sample 28$n$, whereby the dye or biomarker are selectively bound by specific structures/compounds within the bulk tissue sample. Laser energy 40 may then be specifically directed toward the bound regions for subsequent ablation of the marked cells.

Figure 5:
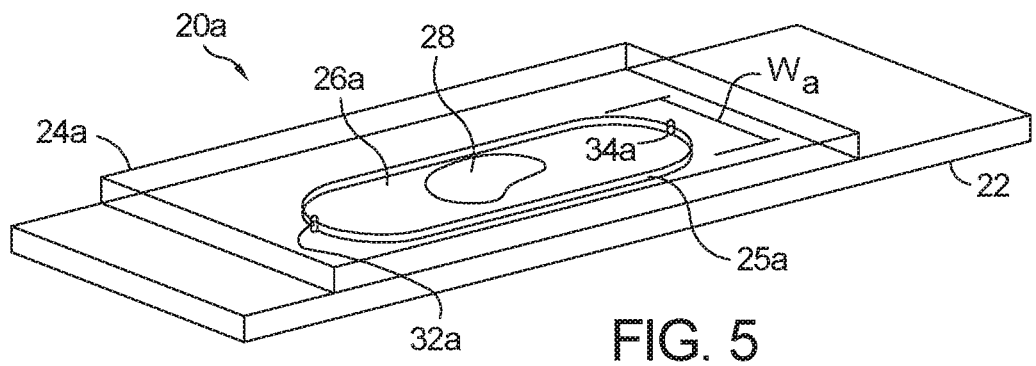
FIG. 5 is an isometric view of another exemplary embodiment of the invention with a single microfluidics recess.
Figure 6:
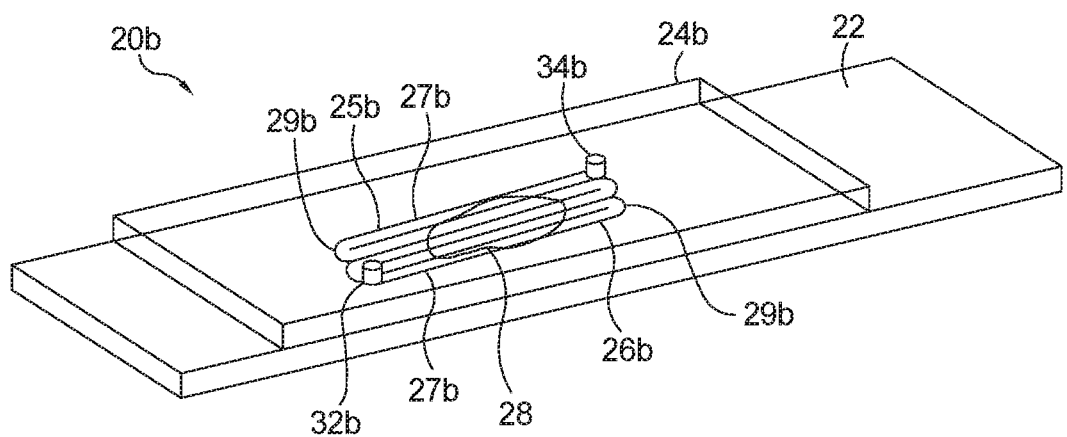
FIG. 6 is an isometric view of another exemplary embodiment of the invention with a single serpentine microfluidics channel.

As generally shown in FIG. 2, channel 26 may have a width W that may be too narrow to overlap an entire tissue sample 28. As such, only that portion of tissue sample 28 overlapped by channel 26 may be potentially ablated and collected as described above. One alternative to providing greater coverage of tissue sample 28 may be through use of a microfluidic device 20$a$ generally shown in FIG. 5. In accordance with an aspect of the present invention, microfluidic substrate 24$a$ may be fabricated to include a wider recess 25$a$, such that, upon coupling microfluidic substrate 24$a$ with glass slide 22, a channel 26$a$ may be formed having a wider width $W_a$ when compared to channel 26 of microfluidic device 20. Without limitation thereto, width $W_a$ may be selected to be between about 1 mm and about 25 mm. Channel 26$a$ may include a single inlet end 32$a$ and a single outlet end 34$a$. As a result, more or all of sample 28 may be in fluid communication with channel 26$a$.

FIGS. 6-12 show alternative microfluidic devices 20$b$-20$f$ configured to provide greater tissue sample overlap while using microfluidic channel(s) having widths less than about 1 mm. Discussing each in turn, and with immediate reference to FIG. 6, microfluidic device 20$b$ may comprise glass slide 22 coupled to microfluidic substrate 24$b$. Microfluidic substrate 24$b$ may be configured to include a serpentine recess 2$b$, which, when coupled to glass slide 22, forms a serpentine channel 26$b$ having an inlet end 32$b$ and an outlet end 34$b$. In one aspect of the invention, the serpentine channel includes alternating linear channel segments 27$b$ and curved channel segments 29$b$ wherein linear channel segments 27$b$ are arranged in parallel relation to one another. Serpentine channel 26$b$ may be configured to overlap all or a significant portion of tissue sample 28. In this manner, fluid may flow from inlet end 32$b$ to outlet end 34$b$ while the laser (not shown) may selectively cavitate the fluid and ablate selected cells as described above, but over a larger field while also providing improved fluid dynamics than when using a wide channel.

Figure 7:
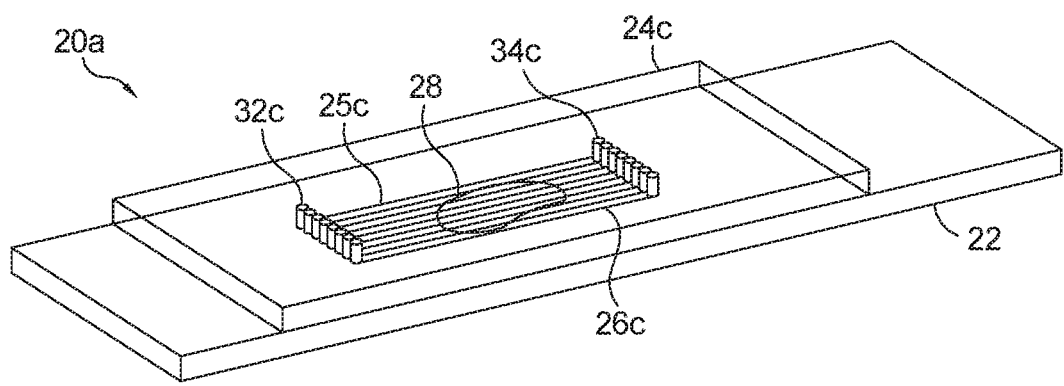
FIG. 7 is an isometric view of yet another exemplary embodiment of the invention with a plurality of parallel microfluidic channels.

Turning now to FIG. 7, microfluidic device 20$c$ may comprise glass slide 22 coupled to microfluidic substrate 24$c$. Microfluidic substrate 24$c$ may be configured to include a plurality of recesses 25$c$ arranged in spaced parallel relation to one another. When coupled to glass slide 22, microfluidic substrate 24$c$ thus forms a plurality of parallel spaced channels 26$c$, each respective channel 26$c$ having a respective inlet end 32$c$ and an outlet end 34$c$. The collective channels 26$c$ may be configured to overlap all or a significant portion of tissue sample 28. Depending upon the location of the tissue sample selected to be sampled through laser cavitation and ablation as described above, fluid may flow from a respective inlet end 32$c$ to a respective outlet 34$c$ of the overlapping channel 26$c$ within the array of parallel channels. As such, a larger field of tissue sample 28 may be interrogated while also providing improved fluid dynamics than when using the wide channel and while also reducing fluid travel length, resultant back pressure issues, and increased sample collection times when using long channels.

Figure 8:
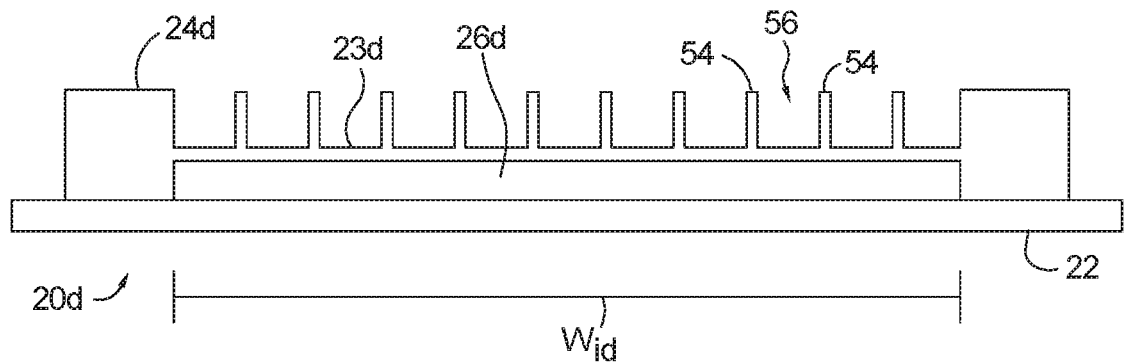
FIG. 8 is an diagrammatic section view of an exemplary addressable microfluidic substrate within an embodiment of the invention, the substrate shown non-actuated.
Figure 9:
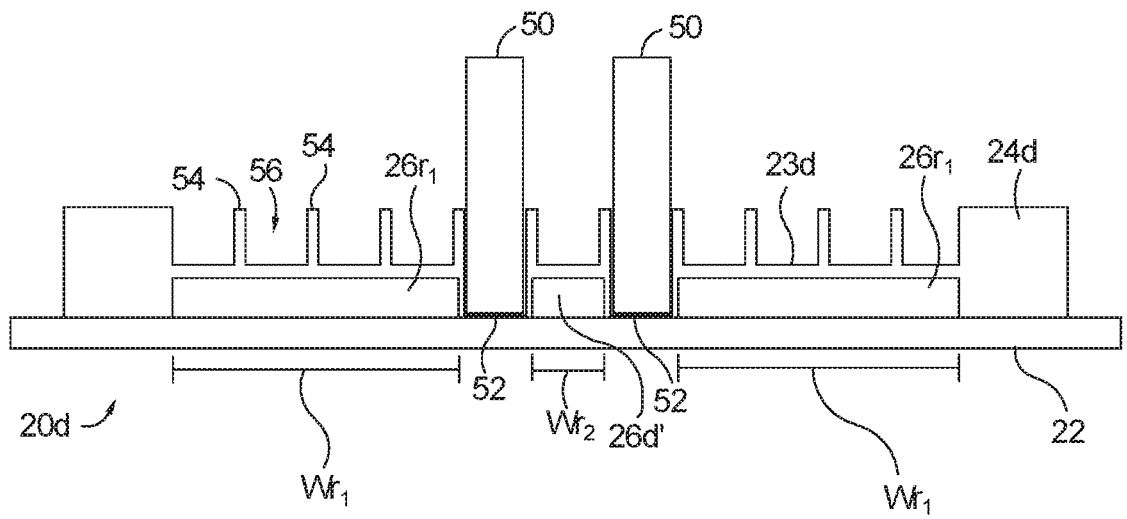
FIG. 9 is a diagrammatic section view of the apparatus shown in FIG. 8 with the substrate actuated by selective plungers.

FIGS. 8 and 9 generally depict a microfluidic device 20$d$ including a glass slide 22 coupled to microfluidic substrate 24$d$ which may be comprised of a selectively actuatable membrane 23$d$ defining an initial channel 26$d$ having an initial width $W_{id}$ (FIG. 7). Actuatable membrane 23$d$ may be mechanically addressable so as to reduce the channel width of channel 26$d$. By way of example and without limitation solely thereto, actuatable membrane 23$d$ may be actuated by one or more plungers 50 whereby a plunger 50 imparts a force upon a selected portion 52 of microfluidic substrate 24$d$ so as to direct selected portion 52 into touching engagement with slide 22. In this manner, initial channel 26$d$ is segregated into two or more reduced channels 26$_{r1}$ and 26$_{r2}$ having a reduced width, such as width $W_{r1}$ and $W_{r2}$ as shown in FIG. 9.

As also shown in FIG. 9, two or more plungers 50 may be employed to define the reduced channels (e.g., $W_{r1}$, $W_{r2}$). In this manner, and as shown in FIG. 9, a microfluidic channel 26$d'$ may be selectively created, where channel 26$d'$ is selected to overlap with a portion of the tissue sample (not shown, see e.g., FIGS. 2 and 6) which will be subjected to impingement by the laser and resultant cavitation and cell ablation as described above. In accordance with one aspect of the present invention, microfluidic substrate 24$d$ is a flexible yet resilient member whereby initial channel 26$d$ will substantially reform following removal of downward pressure from plunger(s) 50. Plunger(s) 50 may then be relocated over another portion of microfluidic substrate 24$d$ so as to form another microfluidic channel over another selected portion of the tissue sample. To assist in locating plunger(s) 50, microfluidic substrate 24$d$ may include a plurality of upwardly extending ribs 54 arranged in uniform spaced parallel relation so as to define a plurality of alternating grooves 56. Grooves 56 may be proportioned to receive plunger(s) 50 so as to enable selective actuation of plunger(s) 50 to form a plurality of microfluidic channels having a substantially constant width, such as $W_{r2}$. As a result, all or a substantial portion of the tissue sample may be interrogated by sequentially creating serial channels 26$d'$.

Figure 10:
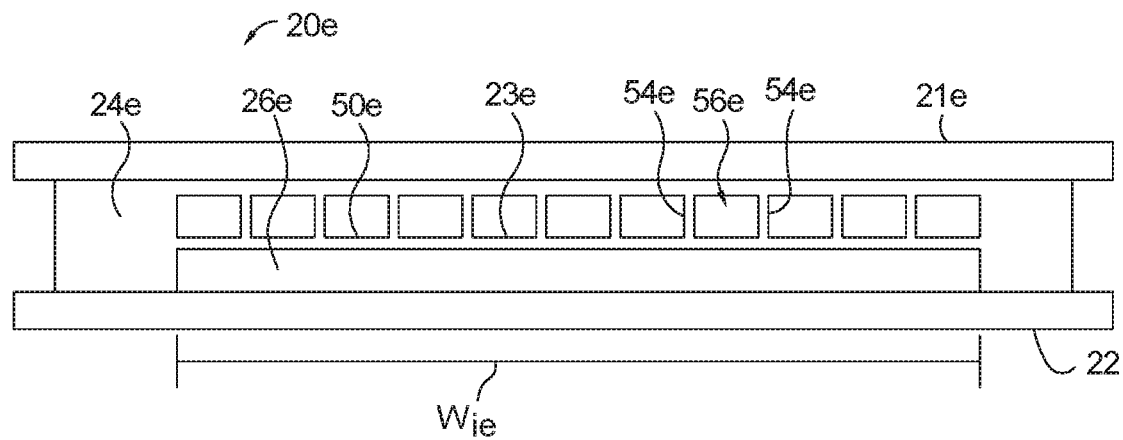
FIG. 10 is a diagrammatic section view of another exemplary addressable microfluidic substrate shown non-actuated.
Figure 11:
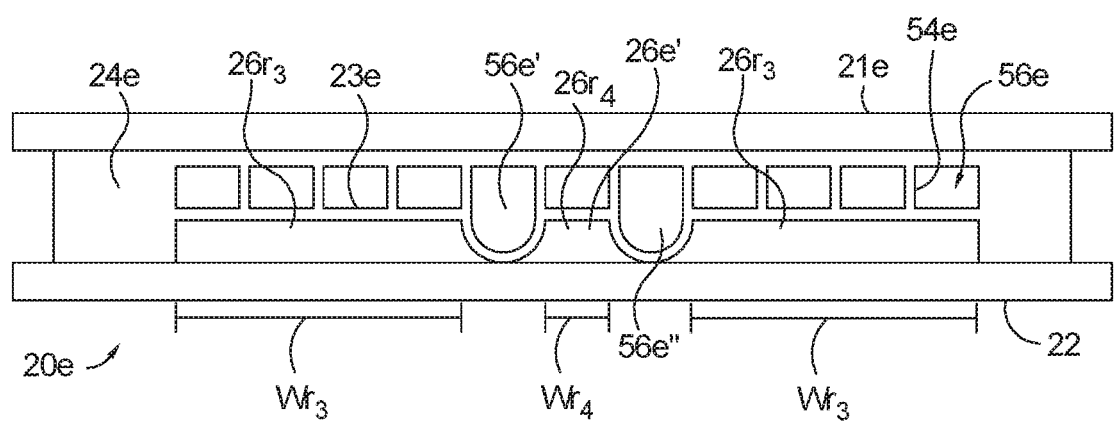
FIG. 11 is a diagrammatic section view of the apparatus shown in FIG. 10 with the substrate actuated by selective pressurization of the substrate.

FIGS. 10 and 11 generally depict a microfluidic device 20$e$ including a bottom glass slide 22, a top cover 21$e$ and a microfluidic substrate 24$e$ coupled therebetween. Microfluidic substrate 24$e$ may be comprised of a selectively actuatable membrane 23$e$ defining an initial channel 26$e$ having an initial width $W_{ie}$ (FIG. 10). Actuatable membrane 23$e$ may further define a plurality of conduits 56$e$ separated by membrane sidewalls 54$e$. Each conduit 56$e$ may be selectively, individually addressable so as to reduce the channel width of channel 26$e$. By way of example and without limitation solely thereto, actuatable membrane 23e may be pneumatically actuated by a high pressure air source (not shown) so as to impart a force upon a selected conduit 56e to thereby expand a selected portion 50e of actuatable membrane into touching engagement with slide 22. In this manner, initial channel 26e may be segregated into two or more reduced channels $26_{r3}$ and $26_{r4}$ having a reduced width, such as width $W_{r3}$ and $W_{r4}$ as shown in FIG. 11.

As also shown in FIG. 11, two or more conduits 56e (e.g., 56e'/56e") may be expanded to define the reduced channels (e.g., $W_{r3}$, $W_{r4}$). In this manner, and as shown in FIG. 11, a microfluidic channel 26e' may be selectively created, where channel 26e' is selected to overlap with a portion of the tissue sample (not shown, see e.g., FIGS. 2 and 7) which will be subjected to impingement by the laser and resultant cavitation and cell ablation as described above. In accordance with one aspect of the present invention, microfluidic substrate 24e is a flexible yet resilient member whereby initial channel 26d will substantially reform following removal of any applied high pressure air. A second conduit 56e or conduit pair 56e'/56e" may then be pneumatically actuated so as to form another microfluidic channel over another selected portion of the tissue sample. As a result, all or a substantial portion of the tissue sample may be interrogated.

Figure 12:
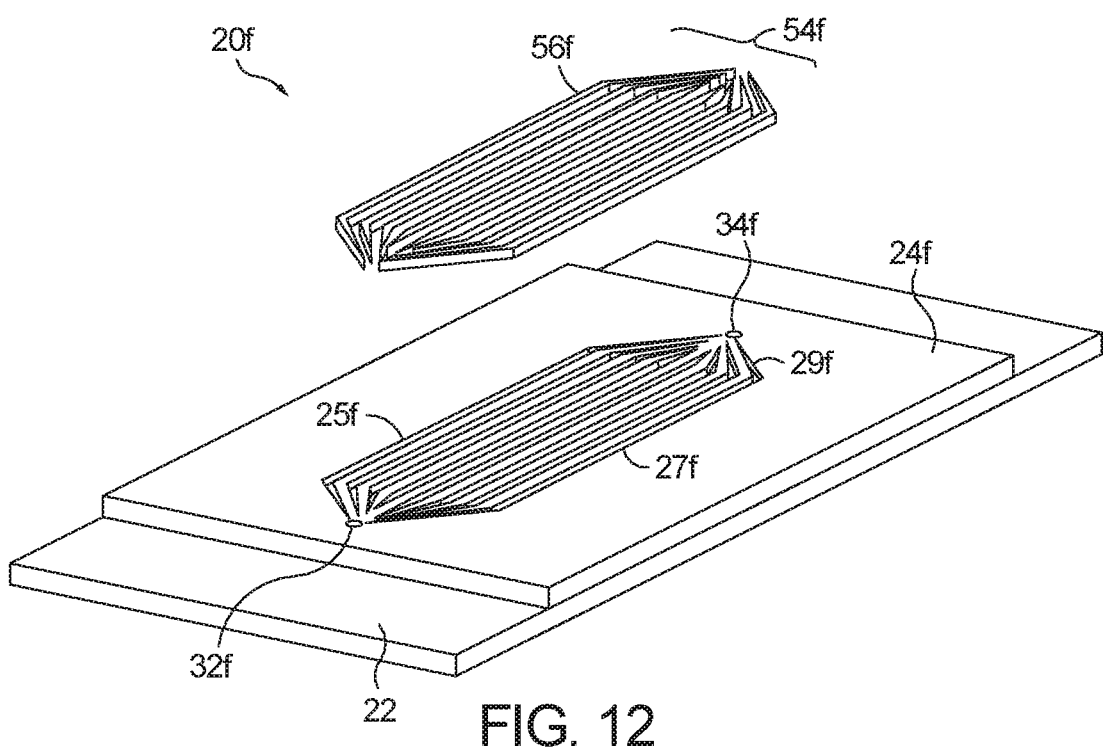
FIG. 12 is a diagrammatic section view of yet another exemplary addressable microfluidic substrate actuated by mechanical channel insert actuators.

Turning now to FIG. 12, microfluidic device 20f may comprise glass slide 22 coupled to microfluidic substrate 24f. Microfluidic substrate 24f may be configured to include a plurality of recesses 25f having linear channel segments 27f arranged in spaced parallel relation to one another and angled end portions 29f in communication with either common inlet end 32f or common outlet end 34f. A top cover (not shown) includes a set 54f of channel inserts 56f (elevated for clarity) such that, when coupled to microfluidic substrate 24f, the top cover and glass slide 22 form a plurality of spaced channels similar to channel 26. The collective channels may be configured to overlap all or a significant portion of tissue sample 28 affixed to glass slide 22. Depending upon the location of the tissue sample selected to be sampled through laser cavitation and ablation as described above, a selected channel 26f may enable fluid flow from inlet end 32f to outlet 34f. In one aspect of the invention, channel insert set 54f may be configured to socket each channel insert 56f within its respective corresponding channel, whereby a selected channel insert 56f may then be actuated to lift from the selected channel thereby permitting fluid flow through only that selected channel. Alternatively, channel insert set 54f may be configured to lie above recesses 25f so as to define a plurality of open channels. In operation, all but one channel insert 56f may then be actuated to block fluid flow within its respective channel. In this manner, only one channel will remain open such that any fluid flow would be directed into that open channel. As a result, all or a substantial portion of the tissue sample may be interrogated by sequentially selecting which respective channel is open at one time.

Figure 13:
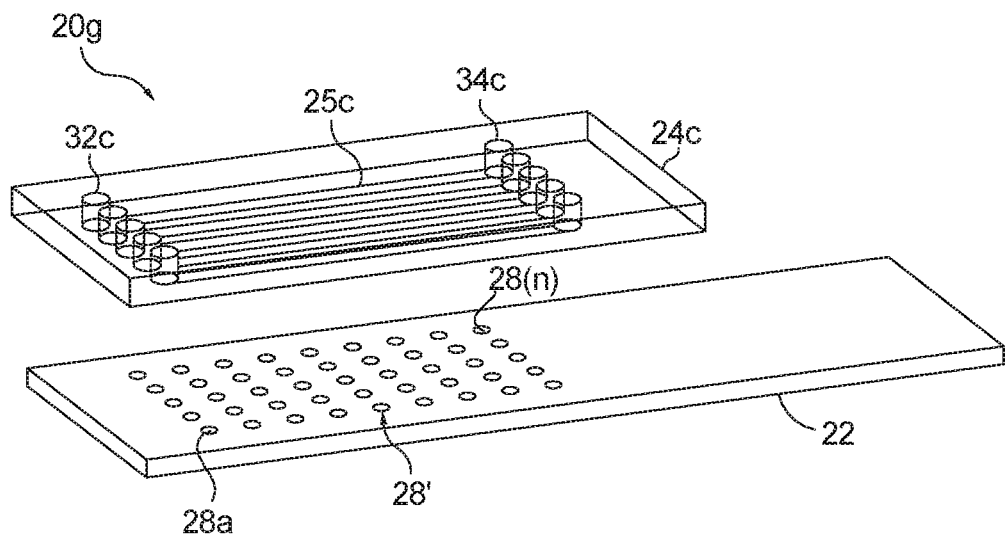
FIG. 13 is a diagrammatic section view of another exemplary microfluidic channel in operation with a multiple tissues.
Figure 14:
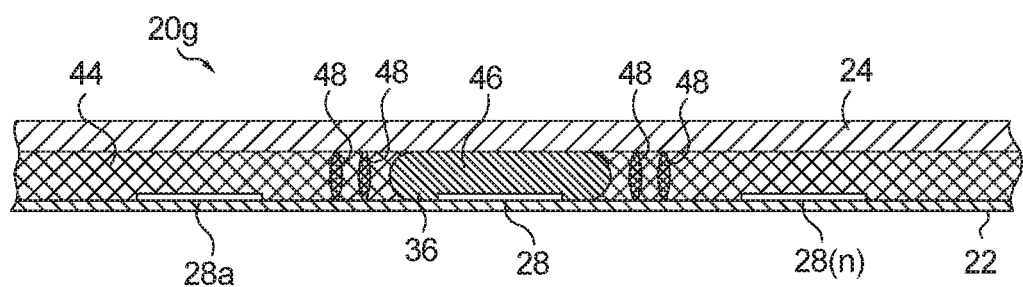
FIG. 14 is a diagrammatic section view of an exemplary microfluidic channel, such as that shown in FIG. 13, in operation with multiple tissues.

Heretofore, microfluidic devices 20-20f have been described for use with a single tissue sample 28. However, it should be understood by those skilled in the art that the above devices may be suitable for use with multiple tissue samples affixed to a single slide. With attention to FIGS. 13 and 14, an exemplary microfluidic device 20g for use with an array 28' of multiple tissue samples 28a-28(n) is shown. As can be seen in FIG. 13, glass slide 22 may be configured to receive an array 28' of tissue sample 28a-28(n), such as in a grid-like pattern. A microfluidic substrate, such as but not limited to microfluidic substrate 24c, may be couple to glass slide 22 so as to form channels 26c, as described above (see FIG. 7). Each individual sample 28a-28(n) may be sequentially interrogated by selectively flowing fluid(s), such as a first fluid 36, a fluid slug 46 of second fluid 44 and wash droplets of a third fluid 48 (see FIG. 14), from a respective inlet end 32c to the corresponding outlet end 34c of a channel 26c which overlaps the particular sample 28 being interrogated. A laser (i.e., laser 38) may then impinge upon the fluid within channel 26c as described above so as to cause fluid cavitation and cell ablation from the tissue sample. Each tissue sample (or portion thereof) may then be collected within a dedicated sample container at outlet end 34c as described above. In this manner, multiple cell samples may be selectively extracted and collected with minimal to no cross contamination between samples.

Figure 15:
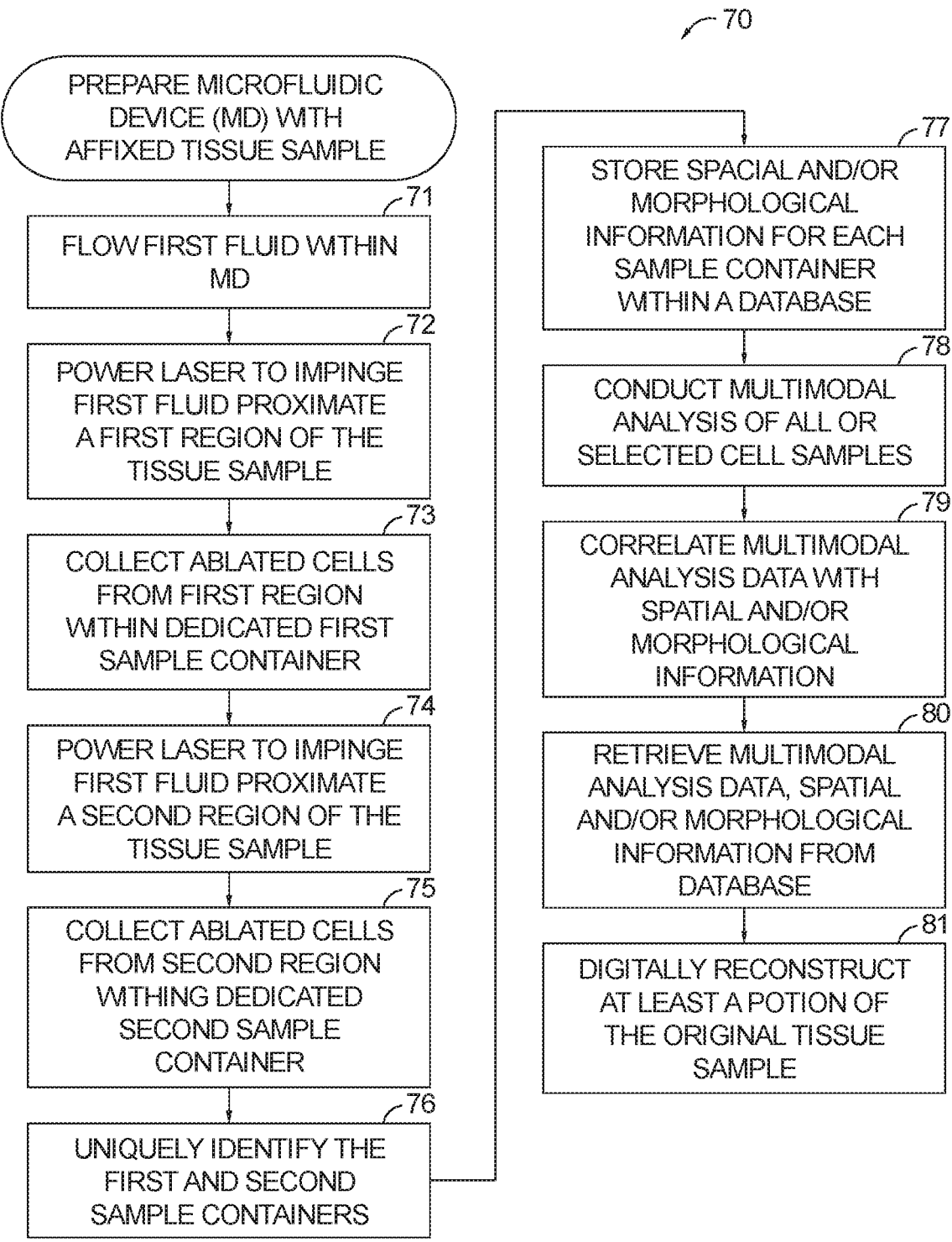
FIG. 15 is a flowchart of a method for dissecting and analyzing cell samples in accordance with an aspect of the invention.

As generally indicated in FIG. 15, a method 70 for dissecting and collecting one or more cells from a tissue sample affixed within a microfluidic device may comprise: a) flowing a first fluid through the channel with a fluid flow from the inlet end to the outlet end (step 71); b) powering a laser to direct laser energy into the channel to impinge upon the first fluid proximate a first region of the tissue sample and cause fluid cavitation to thereby ablate a first set of one or more cells from the tissue sample (step 72); and c) collecting the first set of one or more cells within a first sample container coupled to the outlet end (step 73). The method may further include: d) powering the laser to direct laser energy into the channel to impinge upon the first fluid proximate a second region of the tissue sample and cause fluid cavitation to thereby ablate a second set of one or more cells from the tissue sample (step 74); and e) collecting the second set of one or more cells within a second sample container coupled to the outlet end (step 75). Still further, the method may comprise: f) uniquely identifying the first and second sample containers to conserve spatial and/or morphological information of the respective first and second sets of one or more cells relative to the fixed tissue sample (step 76); and g) storing the spatial and/or morphological information of the respective first and second sets of one or more cells within in a database (step 77). Additional steps may include: h) performing molecular analysis on one or both of the first and second sets of one or more cells to create cell data (step 78); and i) correlating the cell data with the respective spatial and/or morphological information of the respective first and/or second sets of one or more cells to create a compiled data file for each cell or group of cells within the first and second sets of one or more cells (step 79), as well as j) retrieving at least one of the spatial and/or morphological information, the cell data or the compiled data from the database (step 80); and k) digitally reconstructing at least a portion of the tissue sample using at least one of the spatial and/or morphological information, the cell data and the compiled data (step 81).

Figure 16:
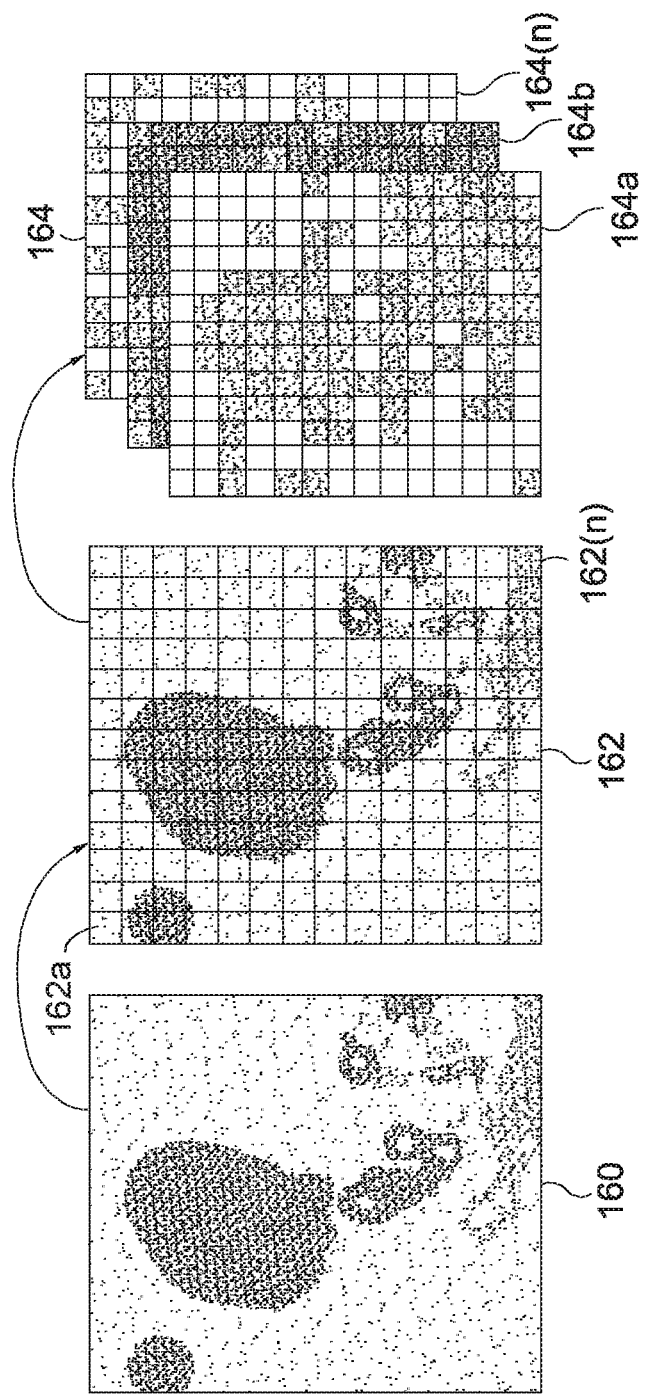
FIG. 16 is an exemplary multimodal mapping flow diagram illustrating microdissection for qubit study in accordance with an aspect of the invention.

With the above method 70 outlined in FIG. 15, attention is now directed to FIG. 16 which illustrates a multimodal mapping flow diagram illustrating microdissection for qubit study in accordance with one aspect of the present invention. Slide 160 includes a tissue sample (such as tissue sample 28, which in this exemplary case may be a histological FFPE sample). Prior to dissection and collection, slide 160 may be imaged, such as through a microscope, where slide 160 may then be subdivided into areas by grid or custom shapes as generally indicated by subdivisions 162a-162(n) in microdissection 162. Such subdivision may be computer-implemented or computer-aided according to presets, manual selection or an algorithm as is known in the art. Each defined subdivision 162a-162(n), or any specifically identified subdivision(s) may then be dissected/ablated and delivered for molecular analysis as described above. Each subdivision may be segregated and labeled whereby the analytical results may be correlated to the original location of the subdivision within the sample slide. As a result, each subdivision may be visualized as map 164. For those analyses employing more than one biomarker (see above with regard to FIG. 4), multiple maps 164a through 164(n) may be generated corresponding to different biomarkers. In this manner, maps may be displayed preserving the original spatial locations of the dissected samples and images. By way of example and not to be limited thereto, maps 164a-164(n) may be heat maps, wherein the magnitude of shading within each grid correlates to magnitude of detection. That is, a darker grid location may indicate a higher or lower magnitude that a lighter shaded location. This may be generally referred to as a 2-dimensional analysis.

Figure 17:
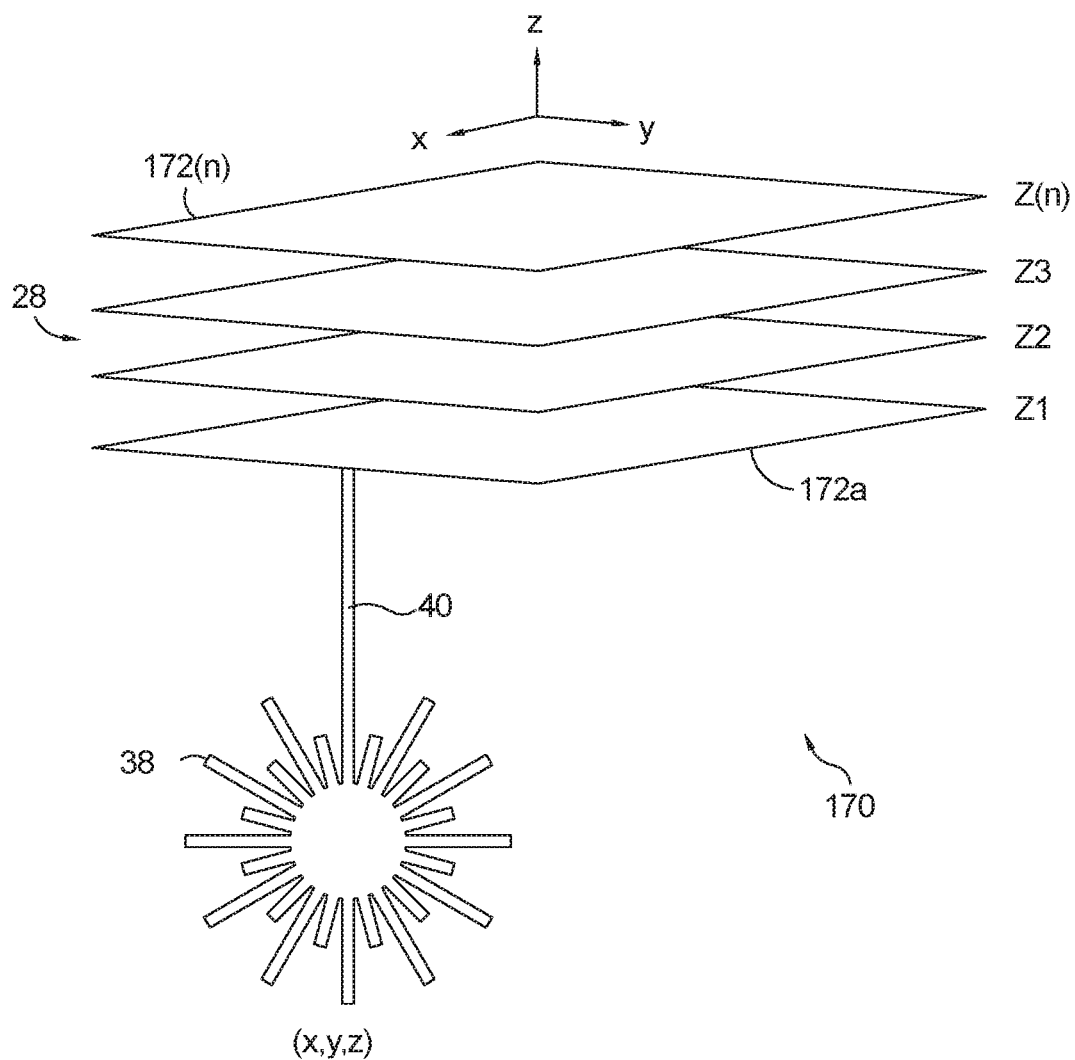
FIG. 17 is an exemplary multimodal region of interest dissecting method illustrating microdissection in three dimensions for qubit study in accordance with an aspect of the invention.

Turning now to FIG. 17, a general schematic of a 3-dimensional dissection method is generally indicated by reference numeral 170. Dissection 170 employs similar techniques as described above with regard to FIG. 16, except wherein slide 160 was confined to x- and y-directions, microdissection 170 may be expanded in the z-direction. To that end, microdissection 170 may comprise layered imaging planes 172a-172(n). Tissue sample 28 may then be imaged on parallel planes Z1-Z(n) to determine regions of interest. Such subdivision may be computer-implemented or computer-aided according to presets, manual selection or an algorithm as is known in the art. Regions may range in size from bulk cell to single cell to fraction of cells. Dissection with laser 38, as described above, may discretely ablate targeted cells while recording the x, y, z coordinates of each ablation such that the ablated cells may be correlated to their original location (x, y and z) within the sample.

Figure 18:
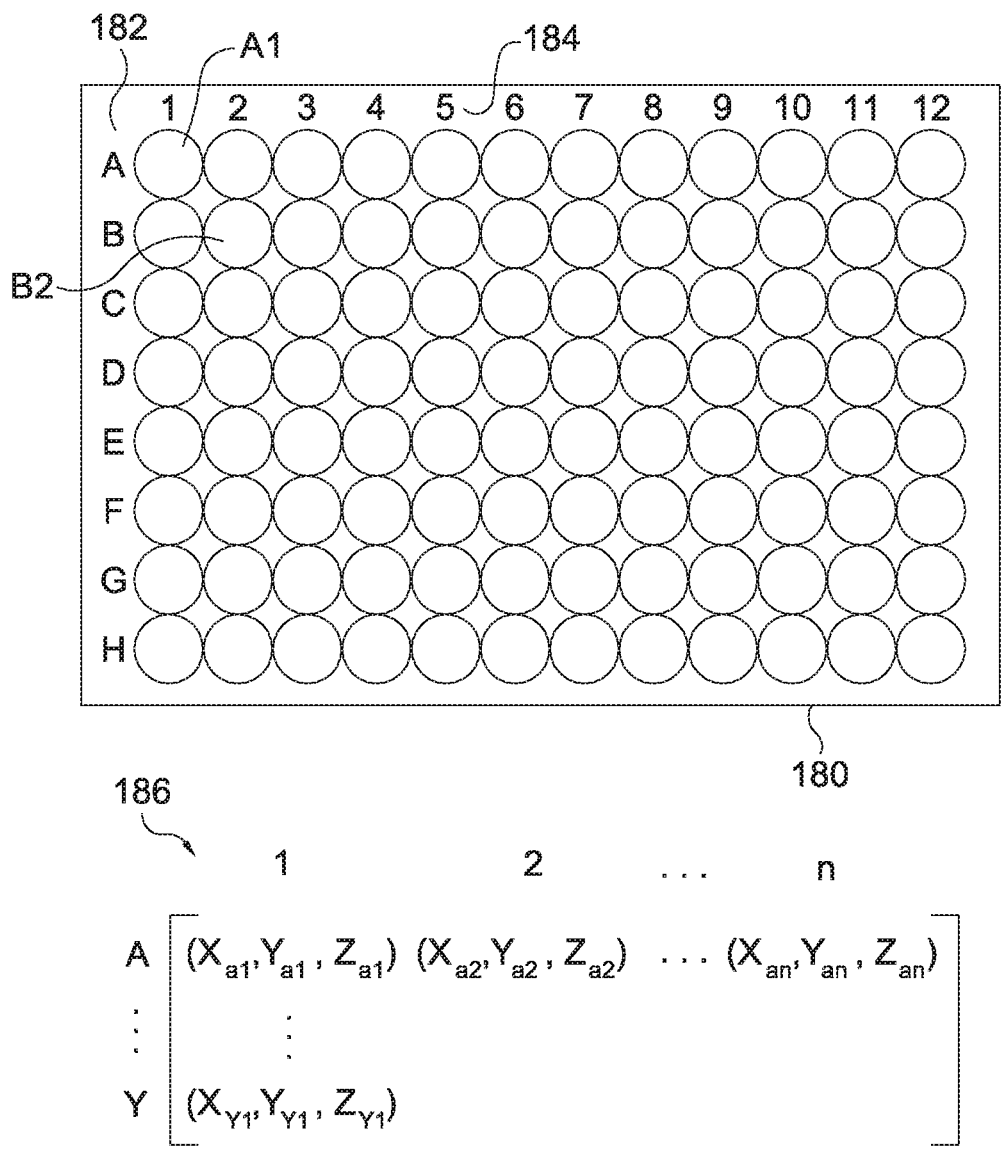
FIG. 18 is an exemplary multimodal region of interest sorting-and-addressing method suitable for use with the methods shown in FIGS. 16 and 17.

As shown in FIG. 18, a method of sorting and addressing cell samples (such as via fluid slugs 46 described above) for qubit study in accordance with the present invention may utilize a 96-well plate 180. Well plate 180 may be include well coordinate rows 182 (from A through H) and columns 184 (from 1 through 12) to define specific individual wells (i.e., sample containers), such as A1, B2, etc. Well plate 180 may communicate with a well correlation database 184 as is known in the art. Dissected samples are deposited into the wells (which may also include vessels or tubes or vials) and coordinates 182/184 are correlated to the sample dissection coordinates x-y-z such that database 184 is populated accordingly.

Figure 19:
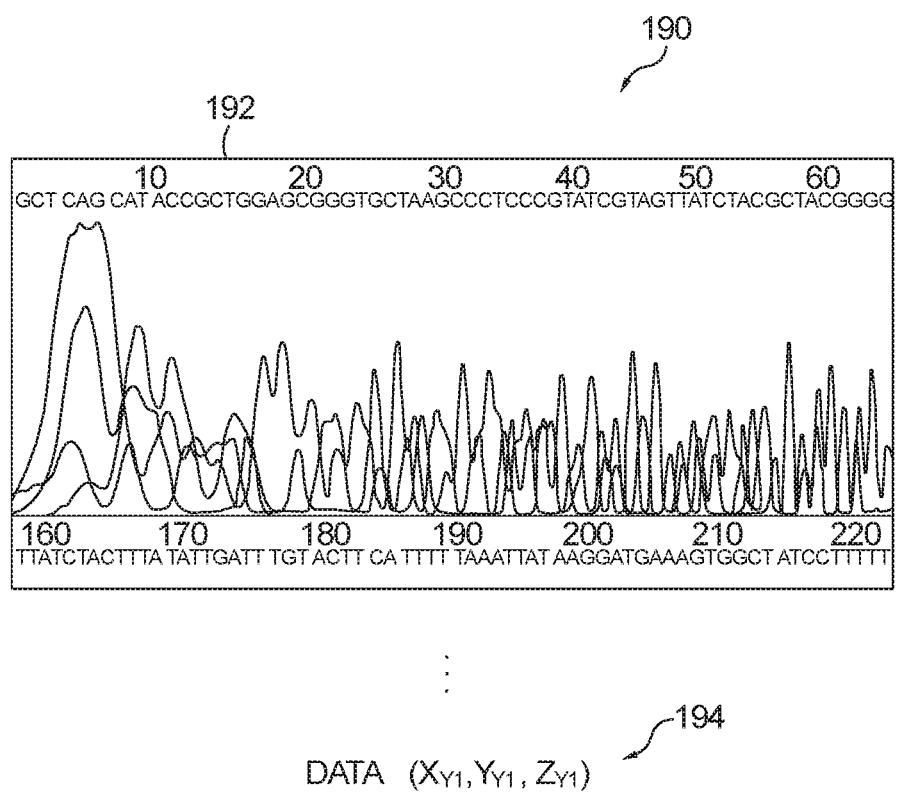
FIG. 19 is an exemplary multimodal molecular analysis method for use with cell samples produced in accordance with the methods shown in FIGS. 15-18.

With reference to FIG. 19, a multimodal molecular analysis method 190 includes a molecular analysis output 192 and database 194. All or selected samples from well plate 180 may be independently analyzed, including but not limited to analyses of molecular content and composition using exemplary techniques such as qRT-PCR, RNA Seq, DNA Seq, NGS, etc. Analytical results are evaluated on plot 192 or similar (hysteretic loop) output display and an analytical results database 194 is populated accordingly. Database 194 may then be correlated with data base 186 and its spatial coordinate database x-y-z. As a result, analytical data may be directly attributable to a specific location within the original tissue sample.

Figure 20:
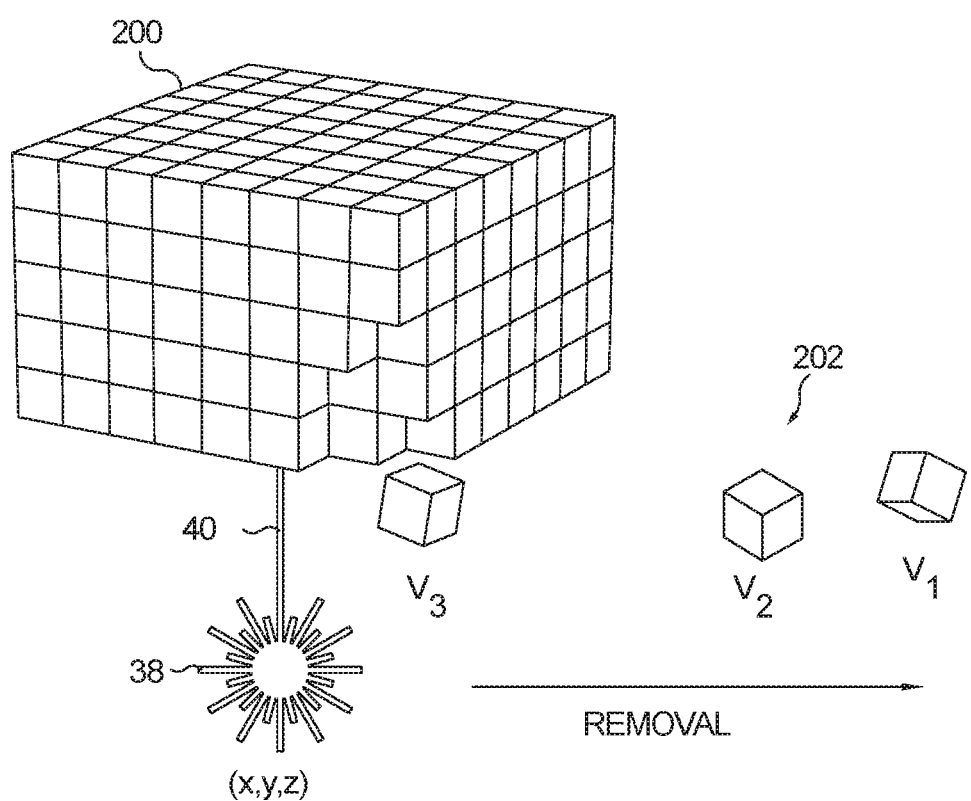
FIG. 20 is an exemplary 3-D qubit separation from voxel process in accordance with an aspect of the invention.
Figure 21:
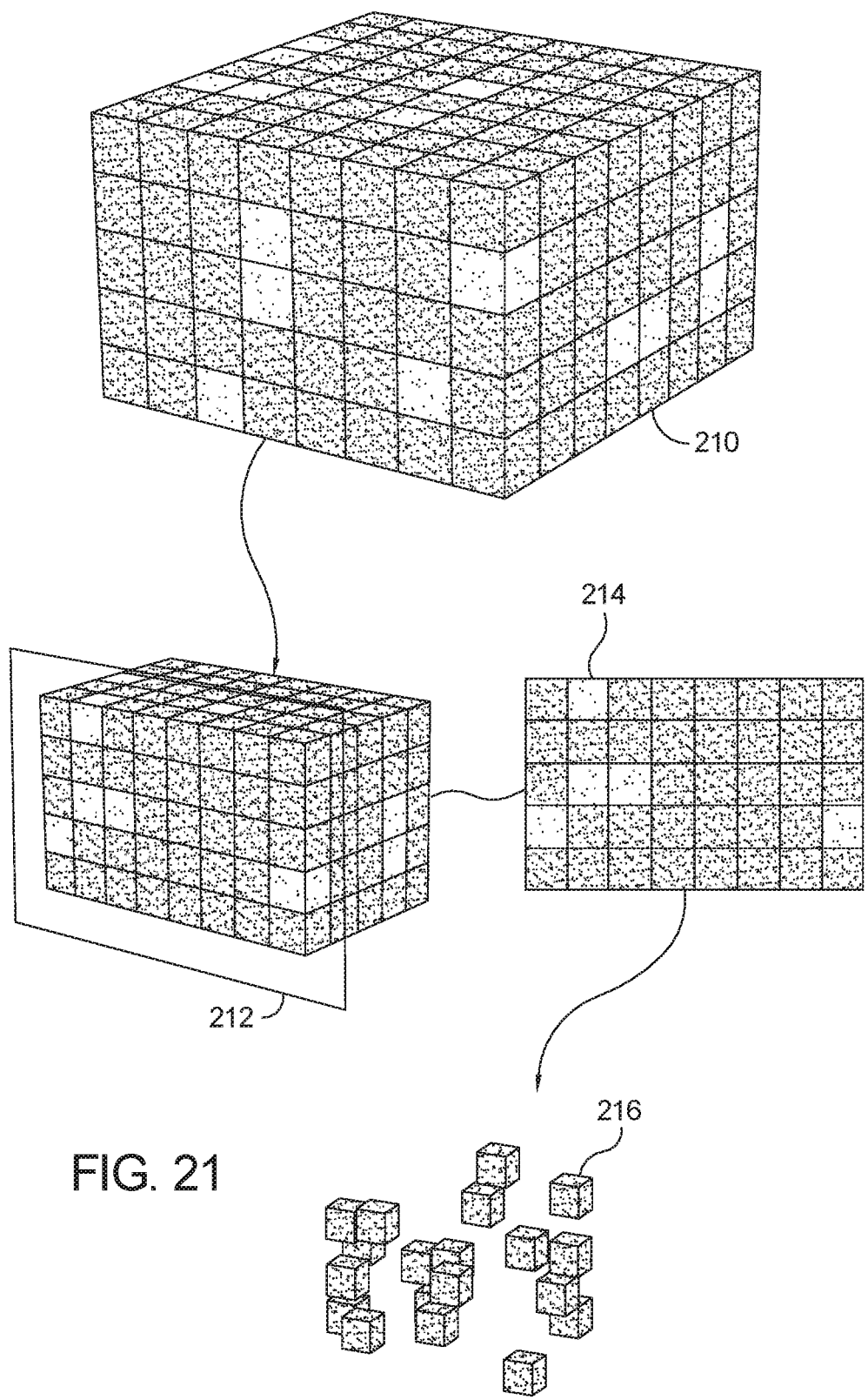
FIG. 21 is another exemplary voxel visualization process reconstructed from qubits in accordance with an aspect of the invention.

FIG. 20 generally illustrates an exemplary 3-D qubit separation from voxel process as described above with reference to FIGS. 17-19. Voxel 200 may be subdivided into qubits 202 (V1 V2 and V3) which have designated x, y, and z coordinates. Voxel 200 (all or a portion of tissue sample 28 under study) may be subdivided and dissected by laser 38 and laser energy 40 as described above. The spatial coordinates (x, y and z) for the laser is known and tracked such that, as each individual qubit 202 (V1, V2, V3) is ablated and transported sequentially as described above, the location of each dissected subdivision within the original tissue sample is known and tracked by spatial database. Each qubit 202 may then be sorted into respective wells of plate 182 for molecular analysis 190 to obtain database 192 as described above. Visual presentation of analytical results may take the form of a heat map similar to that described above with regard to FIG. 16. However, as voxel 200 possess information in three dimensions, voxel visualization reconstructed from qubits, may generally include a voxel computer model 210 which may be displayed, by example, along cross-sectional plane 212, as a planar layer 214. Planar layer 214 may by further dissected into fragments 216 (qubits data). In this manner, model 210 may be sliced layer-by-layer in any desired sectional orientation, with each layer 214 may be further broken down to qubits 214. As a result, model 210 may be a true computer data representation of physical voxel 200 wherein model 210 may be built from databases x-y-z (laser location information), 163 or 186 (tissue sample location within 96-well plate), and 194 (analytical data corresponding to location within 96-well plate).

As will be appreciated by those skilled in the art, the digitalized model 210 will be suitable to study long after the physical samples are gone, destroyed, discarded or degraded. Moreover, model 210 may be shared by scientists and practitioners as digital files may be electronically distributed across the globe wherein physical specimens were solely within the domain of the research/clinical laboratory possessing those samples. To that end, all information encoded within model 210, along with all data within databases 163, 186 and 194, may be stored on a cloud-based data storage device. The cloud-based data storage device may be an access-controlled, shared-computing device accessible wirelessly. As a result, samples may be studied by a host of remote experts and practitioners where they may share their findings instantly, even long after the physical samples are destroyed by nature or on purpose in laboratories. This may globalize currently local biological tissue cell research, advancing microbiology related to tumor recognition and study.

The present invention is described above with reference to a preferred embodiment. However, those skilled in the art will recognize that changes and modifications may be made in the described embodiment without departing from the nature and scope of the present invention. For instance, employing bidirectional microchannel arrays spatially separated but connected by across microfluidic holes (sequencer) is considered obvious modification to employing unidirectional micro-channels and thus hereby considered to be within the scope of the invention.

Various further changes and modifications to the embodiment herein chosen for purposes of illustration will readily occur to those skilled in the art. To the extent that such modifications and variations do not depart from the spirit of the invention, they are intended to be included within the scope thereof. Accordingly, it is intended that the invention not be limited to the described embodiments, but will have full scope defined by the language of the following claims.

What is claimed is:

1. A method for dissecting and collecting one or more cells from a tissue sample fixed to a microfluidic device, wherein said microfluidic device includes a channel having an inlet end and an outlet end for flowing a first fluid therethrough and wherein said tissue sample is in fluid communication with said channel, the method comprising:

a) flowing said first fluid through the channel with a fluid flow from the inlet end to the outlet end;
b) communicating said tissue sample with said flowing first fluid;
c) powering a laser to direct laser energy into the channel to impinge upon the first fluid proximate a first region of the tissue sample at a distance from a surface of said tissue sample wherein said tissue sample is exposed to little or no radiation from said laser energy;
d) causing fluid cavitation of said flowing first fluid to thereby hydrodynamically ablate a first set of one or more cells from the tissue sample;
e) capturing said ablated first set of one or more cells within said flowing first fluid for transporting to said outlet end of said channel; and
f) collecting the first set of one or more cells within a first sample container coupled to the outlet end.

2. The method in accordance with claim 1 further comprising:
g) flowing a second fluid within the channel wherein the first fluid forms discretized fluid slugs comprised of the first fluid.

3. The method in accordance with claim 2 wherein the laser is powered when a respective fluid slug of the first fluid communicates with the first region of the tissue sample, and wherein the laser is unpowered when the second fluid communicates with the first region of the tissue sample.

4. The method in accordance with claim 2 wherein the first fluid is an oil and the second fluid is a gas.

5. The method in accordance with claim 2 further comprising: h) flowing a third fluid within the channel, wherein the third fluid forms discretized wash droplets comprised of the third fluid, and wherein the wash droplets are interposed between successive fluid slugs of the first viscous fluid.

6. The method in accordance with claim 5 wherein the first fluid is an oil and the second fluid is a gas, and wherein the third fluid is a liquid immiscible with the oil.

7. The method in accordance with claim 1 wherein the channel is a serpentine channel including alternating linear channel segments and curved channel segments, wherein the linear channel segments are arranged in parallel relation to one another, and wherein each of the linear channel segments are configured to overlap a portion of the tissue sample.

8. The method in accordance with claim 1 wherein the microfluidic device defines a plurality of channels arranged in spaced parallel relation, wherein each of the plurality of channels include a respective inlet end and outlet end, and wherein each of the plurality of channels are configured to overlap a respective portion of the tissue sample.

9. The method in accordance with claim 8 wherein the flow of said first fluid is through one of the plurality of channels at a time.

10. The method in accordance with claim 1 wherein the microfluidic device comprises a planar bottom slide affixed to a microfluidic substrate to define the channel therebetween, wherein the channel includes a length, a width and a depth, and wherein the microfluidic substrate includes a resilient member configured to be addressable to selectively reduce at least a portion of the width of the channel.

11. The method in accordance with claim 10 wherein the resilient membrane is mechanically addressable by a plunger, the plunger actuatable to direct the resilient membrane in touching engagement with the planar bottom slide.

12. The method of claim 10 wherein the resilient membrane is covered by a top cover opposite the planar bottom slide.

13. The method of claim 12 wherein the resilient membrane defines a membrane channel, wherein the membrane channel is actuatable to direct the resilient membrane in touching engagement with the planar bottom slide.

14. The method in accordance with claim 1 wherein the channel overlaps more than one tissue sample, wherein the laser is powered to impinge the first viscous fluid proximate only one tissue sample at a time.

15. The method in accordance with claim 1 further comprising the step of:
g) infusing a solution containing nanoparticles selected to absorb the laser energy prior to powering the laser,
wherein the nanoparticles penetrate a portion of the tissue sample to form a nanoparticle saturated tissue layer, and
wherein the laser energy is directed to the nanoparticle saturated tissue layer so that the nanoparticles absorb the laser energy and ablate the first set of one or more cells from the tissue sample.

16. The method in accordance with claim 1 wherein a target cell within the tissue sample is selectively labeled with a fluorescent dye or biomarker to produce a labeled cell, and wherein the laser energy is directed to the first fluid proximate the labeled cell thereby causing fluid cavitation and ablation of the labeled cell from the tissue sample.

17. The method in accordance with claim 1 further comprising the step of: g) powering the laser to direct laser energy into the channel to impinge upon the first fluid proximate a second region of the tissue sample and cause fluid cavitation to thereby hydrodynamically ablate a second set of one or more cells from the tissue sample; and h) collecting the second set of one or more cells within a second sample container coupled to the outlet end.

18. The method in accordance with claim 17 further comprising the step of effectuating relative movement between the microfluidic device and the laser after collecting the first set of one or more cells within the first sample container and before powering the laser to direct laser energy into the channel to impinge upon the first fluid proximate a second region of the tissue sample.

19. The method in accordance with claim 17 further comprising the steps of:
i) uniquely identifying the first and second sample containers to conserve spatial and/or morphological information of the respective first and second sets of one or more cells relative to the fixed tissue sample; and
j) storing the spatial and/or morphological information of the respective first and second sets of one or more cells within in a database.

20. The method of claim 19 further comprising the steps of:
k) performing molecular analysis on one or both of the first and second sets of one or more cells to create cell data; and
l) correlating the cell data with the respective spatial and/or morphological information of the respective first and/or second sets of one or more cells to create a compiled data file for each cell or group of cells within the first and second sets of one or more cells.

21. The method of claim 20 further comprising the step of:
m) retrieving at least one of the spatial and/or morphological information, the cell data, or the compiled data from the database.

22. The method of claim 21 wherein the database is located in a cloud-based data storage device, and wherein the spatial and/or morphological information, the cell data, and the compiled data are stored and retrieved through a network in communication with the cloud-based data storage device.

23. The method of claim 22 further comprising the step of:
   n) electronically reconstructing at least a portion of the tissue sample using at least one of the spatial and/or morphological information, the cell data, and the compiled data.

24. The method in accordance with claim 17 wherein the first sample container and second sample container are wells within a multi-well plate.

25. The method in accordance with claim 1 further comprising the step of:
   g) optically monitoring ablation of the tissue sample using a microscope.

26. The method in accordance with claim 1 wherein said distance from said surface of said tissue sample is within about 100 nm to about 1 micron.

27. A method for dissecting and collecting one or more cells from a tissue sample fixed to a microfluidic device, wherein said microfluidic device includes a channel having an inlet end and an outlet end for flowing a first fluid therethrough and wherein said tissue sample is in fluid communication with a said channel, the method comprising:
   a) flowing said first fluid through the channel with a fluid flow from the inlet end to the outlet end;
   b) communicating said tissue sample with said flowing first fluid;
   c) directing powered energy into the channel to impinge upon the first fluid proximate a first region of the tissue sample at a distance from a surface of said tissue sample;
   d) causing fluid cavitation of said flowing first fluid to thereby hydrodynamically ablate a first set of one or more cells from the tissue sample by said fluid cavitation;
   e) capturing said ablated first set of one or more cells within said flowing first fluid for transporting to said outlet end of said channel; and
   f) collecting the first set of one or more cells within a first sample container coupled to the outlet end.

* * * * *